United States Patent [19]

Kitano et al.

[11] Patent Number: 4,609,485

[45] Date of Patent: Sep. 2, 1986

[54] BIPYRIMIDINYL DERIVATIVES

[75] Inventors: Kisei Kitano; Tetsuya Ogawa; Yasuyuki Goto, all of Yokohamashi; Naoyuki Yoshida, Kamakurashi, all of Japan

[73] Assignee: Chisso Corporation, Tokyo, Japan

[21] Appl. No.: 700,271

[22] Filed: Feb. 11, 1985

[30] Foreign Application Priority Data

Feb. 17, 1984 [JP] Japan .................. 59-28337
Mar. 9, 1984 [JP] Japan .................. 59-44954

[51] Int. Cl.⁴ .................. C09K 3/34; G02F 1/13; C07D 403/00
[52] U.S. Cl. .................. 252/299.61; 252/299.5; 350/350 R; 350/350 S; 544/296
[58] Field of Search .................. 252/299.5, 299.61; 350/350 R, 350 S; 544/296

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,356,103 | 10/1982 | Schubert et al. | 252/299.61 |
| 4,358,589 | 11/1982 | Schubert et al. | 252/299.61 |
| 4,389,329 | 6/1983 | Boller et al. | 252/299.61 |
| 4,462,923 | 7/1984 | Boller et al. | 252/299.61 |
| 4,510,069 | 4/1985 | Eidenschink et al. | 252/299.61 |
| 4,533,488 | 8/1985 | Fukui et al. | 252/299.61 |

FOREIGN PATENT DOCUMENTS

| | | | |
|---|---|---|---|
| 149238 | 7/1985 | European Pat. Off. | 252/299.61 |
| 2257588 | 6/1973 | Fed. Rep. of Germany | 252/299.61 |
| 3404116 | 8/1985 | Fed. Rep. of Germany | 252/299.61 |
| 60-25973 | 2/1985 | Japan | 252/299.61 |
| 60-109569 | 6/1985 | Japan | 252/299.61 |
| 2092169 | 8/1982 | United Kingdom | 252/299.61 |

OTHER PUBLICATIONS

Nash, J. A. et al., Mol. Cryst. Liq. Cryst., vol. 25, pp. 299-321 (1974).
Schubert, H., Wiss, Z. Univ. Halle, XIX'70M, H. 5, 5.1-18.
Zaschke, H., Advances in Liquid Crystal Research & Applications, ed. Bata, L., Pergamon Press, Oxford, pp. 1059-1074 (1980).
Villiger, A., et al., Z. Naturforsch, vol. 34b, pp. 1535-1541 (1979).
Zaschke, V. H., et al., J. Prakt. Chemie, vol. 315, No. 6, pp. 1113-1120 (1973).
Zaschke, V. H., J. Prakt. Chemie, vol. 317, No. 4, pp. 617-630 (1975).

*Primary Examiner*—Teddy S. Gron
*Attorney, Agent, or Firm*—Leydig, Voit & Mayer, Ltd.

[57] ABSTRACT

A novel bipyrimidinyl derivative which is superior in practical properties and useful as a high temperature liquid crystal component constituting a physically and chemically stable liquid crystal composition is provided, which bipyrimidinyl derivative is a 2,5'-disubstituted-5,2'-bipyrimidinyl expressed by the formula

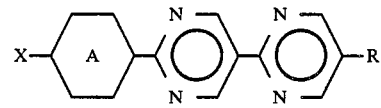

wherein

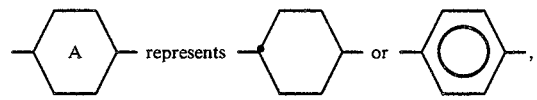

X represents a halogen atom of F, Cl or Br or cyano group or an alkyl group or an alkoxy group each having 1 to 10 carbon atoms and R represents an alkyl group or an alkoxy group each having 1 to 10 carbon atoms.

5 Claims, No Drawings

BIPYRIMIDINYL DERIVATIVES

BACKGROUND OF THE INVENTION

This invention relates to novel organic compounds and more particularly to novel liquid crystal compounds useful as a component for liquid crystal materials.

As is well known, liquid-crystalline compounds have been used in various display devices, utilizing their properties such as dielectric anisotropy, optical anisotropy, etc. in their liquid crystal phases. These display devices refer to liquid crystal display elements having applied the electrooptical effect of liquid crystals or those having applied the thermooptical effect and other optical effects of liquid crystals, and as technics of electronics advance, a large number of liquid crystal compounds have been used for liquid crystal display elements having applied an electric field effect such as twisted nematic effect, guest-host effect, etc.

As for these liquid crystal materials, there is no single compound which is endurable to practical use in the aspect of various characteristics such as mesomorphic range, operation voltage, response properties, etc.; hence practically, several kinds of liquid crystal compounds and if required, non-liquid-crystalline compounds have currently been mixed to obtain materials endurable to use.

SUMMARY OF THE INVENTION

The object of the present invention is to provide compounds which are superior in practical properties as described above and useful as a high temperature liquid crystal component constituting a physically and chemically stable liquid crystal composition.

The present invention resides in 2,5'-disubstituted-5,2'-bipyrimidinyls expressed by the formula

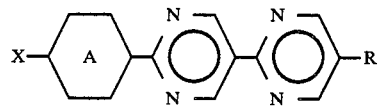

wherein

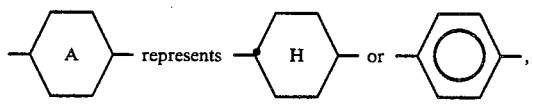

X represents a halogen atom of F, Cl or Br or cyano group or an alkyl group or an alkoxy group each having 1 to 10 carbon atoms and R represents an alkyl group or an alkoxy group each having 1 to 10 carbon atoms, and a composition containing the same.

DETAILED DESCRIPTION OF THE PREFERRED EMBODIMENTS

The compounds of the present invention are liquid crystal compounds of high clearing points which have a positive dielectric anisotropy, a notably large optical anisotropy value, a considerably broad mesomorphic range, mostly a low viscosity for the three-ring compounds, superior stabilities to heat, light, moisture, electricity, etc. necessary for liquid crystal display elements.

Since the compounds of the present invention have a superior compatibility with other liquid crystal compounds, it is possible to mix the former with at least one kind of the latter such as biphenyls, esters, phenyl cyclohexanecarboxylates, phenylcyclohexanes, phenylmetadioxanes, pyrimidines, etc. For example, liquid crystal compositions for TN display elements containing the compounds of the present invention have superior specific features such as a large dielectric anisotropy value, a broad mesomorphic range, a high clearing point, a large optical anisotropy value, etc.; hence the compositions are usable in a broad temperature range and exhibit effects such as improvement in response properties, sharpness, contrast, etc. of display elements.

Preparation of the compounds of the present invention will be described below.

(i) Preparation of compounds of the formula (I) wherein X represents a substituent other than cyano group:

The preparation may be carried out as follows:

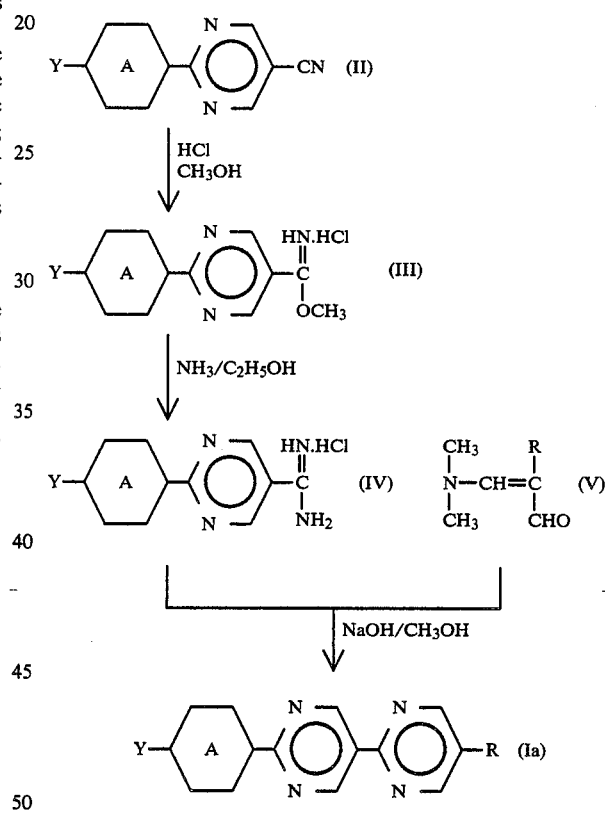

In the above scheme, Y represents a halogen atom of F, Cl or Br, or an alkyl group or an alkoxy group each having 1 to 10 carbon atoms.

First, a 2-substituted-5-cyanopyrimidine (II) is reacted with HCl gas and methanol to obtain an imidoether hydrochloride derivative (III), which is then reacted with $NH_3$ gas in an alcohol solvent to obtain an amidine hydorchloride derivative (IV), followed by subjecting the compound (IV) and an acrolein derivative (V) to condensation-cyclization reaction in the presence of a suitable basic catalyst such as a metal alkoxide, NaOH, 1,8-diazabicyclo[5.4.0]-7-undecene, triethylamine, etc. to obtain an objective compound (Ia) as a compound of the formula (I) wherein X represents a substituent other than cyano group.

(ii) Preparation of compounds of the formula (I) wherein X represents cyano group:

When compounds of the formula (Ia) obtained in the above item (i), wherein Y represents Br are cyanogenated with cuprous cyanide, the objective compounds (Ib) are obtained with a good yield.

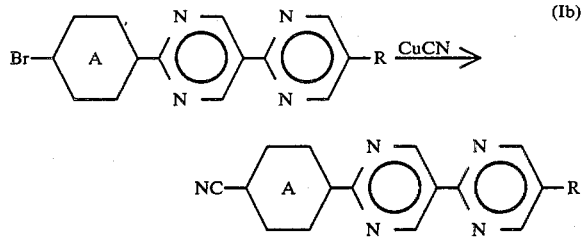

As the compounds of the present invention prepared according to the above methods, the following compounds are enumerated:

(a) Preferable examples of 2-(p-alkylphenyl)-5'-alkyl-5,2'-bipyrimidinyls:

2-(p-propylphenyl)-5'-propyl-5,2'-bipyrimidinyl
2-p-pentylphenyl)-5'-propyl-5,2'-bipyrimidinyl
2-(p-heptylphenyl)-5'-ethyl-5,2'-bipyrimidinyl
2-(p-heptylphenyl)-5'-propyl-5,2'-bipyrimidinyl
2-(p-propylphenyl)-5'-hexyl-5,2'-bipyrimidinyl
2-(p-pentylphenyl)-5'-hexyl-5,2'-bipyrimidinyl
2-(p-heptylphenyl)-5'-hexyl-5,2'-bipyrimidinyl
2-(p-pentylphenyl)-5'-methyl-5,2'-bipyrimidinyl
2-(p-pentylphenyl)-5'-octyl-5,2'-bipyrimidinyl (b) Preferable examples of 2-(p-alkoxyphenyl)-5'-alkyl-5,2'-bipyrimidinyls:

2-(p-propoxyphenyl)-5'-propyl-5,2'-bipyrimidinyl
2-(p-pentyloxyphenyl)-5'-propyl-5,2'-bipyrimidinyl
2-(p-heptyloxyphenyl)-5'-propyl-5,2'-bipyrimidinyl
2-(p-propoxyphenyl)-5'-hexyl-5,2'-bipyrimidinyl
2-(p-pentyloxyphenyl)-5'-hexyl-5,2'-bipyrimidinyl
2-(p-heptyloxyphenyl)-5'-hexyl-5,2'-bipyrimidinyl
2-(p-pentyloxyphenyl)-5'-methyl-5,2'-bipyrimidinyl
2-(p-pentyloxyphenyl)-5'-octyl-5,2'-bipyrimidinyl (c) Preferable examples of 2-(trans-4-alkylcyclohexyl)-5'-alkyl-5,2'-bipyrimidinyls:

2-(trans-4-propylcyclohexyl)-5'-propyl-5,2'-bipyrimidinyl
2-(trans-4-pentylcyclohexyl)-5'-propyl-5,2'-bipyrimidinyl
2-(trans-4-heptylcyclohexyl)-5'-propyl-5,2'-bipyrimidinyl
2-(trans-4-pentylcyclohexyl)-5'-methyl-5,2'-bipyrimidinyl
2-(trans-4-pentylcyclohexyl)-5'-pentyl-5,2'-bipyrimidinyl (d) Preferable examples of 2-(p-alkylphenyl)-5'-alkoxy-5,2'-bipyrimidinyls:

2-(p-propylphenyl)-5'-propoxy-5,2'-bipyrimidinyl
2-(p-propylphenyl)-5'-pentyloxy-5,2'-bipyrimidinyl
2-(p-pentylphenyl)-5'-methoxy-5,2'-bipyrimidinyl
2-(p-heptylphenyl)-5'-methoxy-5,2'-bipyrimidinyl (e) Preferable examples of 2-(p-alkoxyphenyl)-5'-alkoxy-5,2'-bipyrimidinyls:

2-(p-propoxyphenyl)-5'-propoxy-5,2'-bipyrimidinyl
2-(p-propoxyphenyl)-5'-pentyloxy-5,2'-bipyrimidinyl
2-(p-pentyloxyphenyl)-5'-methoxy-5,2'-bipyrimidinyl
2-(p-heptyloxyphenyl)-5'-methoxy-5,2'-bipyrimidinyl (f) Preferable examples of 2-(trans-4-alkylcyclohexyl)-5'-alkoxy-5,2'-bipyrimidinyls:

2-(trans-4-propylcyclohexyl)-5'-propoxy-5,2'-bipyrimidinyl
2-(trans-4-propylcyclohexyl)-5'-pentyloxy-5,2'-bipyrimidinyl
2-(trans-4-pentylcyclohexyl)-5'-methoxy-5,2'-bipyrimidinyl
2-(trans-4-heptylcyclohexyl)-5'-methoxy-5,2'-bipyrimidinyl (g) Preferable examples of 2-(p-halogenophenyl)-5'-alkyl-5,2'-bipyrimidinyls:

2-(p-fluorophenyl)-5'-methyl-5,2'-bipyrimidinyl
2-(p-fluorophenyl)-5'-propyl-5,2'-bipyrimidinyl
2-(p-fluorophenyl)-5'-butyl-5,2'-bipyrimidinyl
2-(p-fluorophenyl)-5'-pentyl-5,2'-bipyrimidinyl
2-(p-fluorophenyl)-5'-hexyl-5,2'-bipyrimidinyl
2-(p-fluorophenyl)-5'-octyl-5,2'-bipyrimidinyl
2-(p-chlorophenyl)-5'-propyl-5,2'-bipyrimidinyl
2-(p-chlorophenyl)-5'-butyl-5,2'-bipyrimidinyl
2-(p-chlorophenyl)-5'-pentyl-5,2'-bipyrimidinyl
2-(p-chlorophenyl)-5'-hexyl-5,2'-bipyrimidinyl
2-(p-bromophenyl)-5'-propyl-5,2'-bipyrimidinyl
2-(p-bromophenyl)-5'-butyl-5,2'-bipyrimidinyl
2-(p-bromophenyl)-5'-pentyl-5,2'-bipyrimidinyl
2-(p-bromophenyl)-5'-hexyl-5,2'-bipyrimidinyl (h) Preferable examples of 2-(p-cyanophenyl)-5'-alkyl-5,2'-bipyrimidinyls:

2-(p-cyanophenyl)-5'-propyl-5,2'-bipyrimidinyl
2-(p-cyanophenyl)-5'-pentyl-5,2'-bipyrimidinyl
2-(p-cyanophenyl)-5'-heptyl-5,2'-bipyrimidinyl (i) Preferable examples of 2-(p-halogenophenyl)-5'-alkoxy-5,2'-bipyrimidinyls:

2-(p-fluorophenyl)-5'-methoxy-5,2'-bipyrimidinyl
2-(p-fluorophenyl)-5'-propoxy-5,2'-bipyrimidinyl
2-(p-chlorophenyl)-5'-methoxy-5,2'-bipyrimidinyl
2-(p-chlorophenyl)-5'-propoxy-5,2'-bipyrimidinyl
2-(p-bromophenyl)-5'-methoxy-5,2'-bipyrimidinyl (j) Preferable example of 2-(p-cyanophenyl)-5'-alkoxy-5,2'-bi-pyrimidinyls:

2-(p-cyanophenyl)-5'-methoxy-5,2'-bipyrimidinyl

The liquid crystal composition of the present invention is characterized by containing at least one member of 2,5'-disubstituted-bipyrimidinyls expressed by the formula (I). More particularly it is obtained by adding 1 to 15% by weight, preferably 2 to 10% by weight of at least one member of 2,5'-disubstituted-5,2'-bipyrimidinyls expressed by the formula (I) to a mixture of compounds selected from liquid-crystalline compounds of phenylcyclohexanes, esters, phenyl cyclohexanecarboxylates, biphenyls, phenylmetadioxanes, pyrimidines, etc.

Examples of liquid-crystalline compounds of phenylcyclohexanes are trans-4-alkyl-(p-cyanophenyl)cyclohexanes, trans-4-alkyl-(p-alkoxyphenyl)cyclohexanes, etc.; examples of liquid-crystalline compounds of esters are p-alkylphenyl p-alkoxybenzoates, p-cyanophenyl p-alkylbenzoates, p-cyanophenyl p-(trans-4-alkylcyclohexyl)benzoates, etc.; examples of liquid-crystalline compounds of phenyl cyclohexanecarboxylates are p-alkylphenyl trans-4-alkylcyclohexanecarboxylates, p-alkoxyphenyl trans-4-alkylcyclohexanecarboxylates, etc.; examples of liquid-crystalline compounds of biphenyls are 4'-alkyl-4-cyanobiphenyls, 4'-alkoxy-4-cyanobiphenyls, etc.; examples of liquid-crystalline compounds of phenylmetadioxanes are 5-alkyl-2-(p-cyanophenyl)-1,3-dioxanes, etc.; and examples of liquid-crystalline compounds of pyrimidines are 5-alkyl-2-(p-cyanophenyl)pyrimidine, 5-cyano-2-(p-alkylphenyl) pyrimidines, etc.

The composition of the present invention is prepared e.g. by adding 5 to 2% by weight of 2,5'-disubstituted- 5,2'-bipyrimidinyls of the formula (I) to 95 to 98% by weight of a mixture of several kinds of trans-4-alkyl(4-cyanophenyl)cyclohexanes.

When the composition of the present invention is used as a material for liquid crystal display elements, it is possible to obtain liquid crystal display elements which can be used stably at higher temperatures and also can be operated at lower driving voltages.

The present invention will be described in more detail by way of Examples, but it should not be construed to be limited thereto.

EXAMPLE 1

2-(p-Pentylphenyl)-5'-propyl-5,2'-bipyrimidinyl

To a solution of NaOH (0.8 g, 0.02 mol) dissolved in dry methanol (30 ml) were added 2-(p-pentylphenyl)-5-pyrimidinecarboxamidine hydrochloride (3.0 g, 0.01 mol) and α-propyl -β-dimethylaminoacrolein (1.4 g, 0.01 mol), followed by boiling with stirring for 2 hours and then distilling off methanol. Water (100 ml) and toluene (100 ml) were added to the reaction residue to extract the product, followed by washing the extraction liquor with water, drying the toluene layer over anhydrous sodium sulfate, distilling off toluene and three times recrystallizing the residual solids from ethanol to obtain the objective 2-(p-pentylphenyl)-5'-propyl-5,2'-bipyrimidinyl (2.0 g, 0.006 mol).

The values of elemental analysis of this compound accorded well with its theoretical values as follows;

| Element | Observed value | Theoretical value |
|---------|---------------|-------------------|
| C | 76.2% | 76.26% |
| H | 7.5% | 7.56% |
| N | 16.1% | 16.17% |

This compound exhibited a crystalline-smectic phase transition point (hereinafter abbreviated to C-S point) of 165° C., a smectic phase-nematic phase transition point (hereinafter abbreviated to S-N point) of 179° C. and a nematic phase-isotropic liquid phase transition point (hereinafter abbreviated to N-I point) of 211° C.

EXAMPLE 2

2-(p-Pentylphenyl)-5'-hexyl-5,2'-bipyrimidinyl was prepared in the same manner as in Example 1. This compound exhibited a C-S point of 160° C., a S-N point of 192°' C. and a N-I point of 194° C.

EXAMPLE 3

2-(Trans-4-pentylcyclohexyl)-5'-propyl-5,2'-bipyrimidinyl was prepared in the same manner as in Example 1. This compound exhibited a C-S point of 156° C., a S-N point of 168° C. and a N-I point of 185° C.

EXAMPLE 4

2-(p-Bromophenyl)-5'-pentyl-5,2'-bipyrimidinyl

To a solution of NaOH (5.1 g, 0.13 mol) dissolved in dry methanol (160 ml) were added to 2-(p-bromophenyl)-5-pyrimidinecarboxamidine hydrochloride (10.0 g, 0.032 mol) and α-pentyl-β-dimethylaminoacrolein (5.4 g, 0.032 mol), followed by boiling with stirring for 2 hours and then distilling off methanol. Water (500 ml) and toluene (500 ml) were added to the reaction residue, followed by extracting the product into the toluene layer, washing the extraction liquor with water, drying the toluene solution with anhydrous sodium sulfate, distilling off toluene and three times recrystallizing the residual solids from ethyl acetate to obtain 2-(p-bromophenyl)-5'-pentyl-5,2'-bipyrimidinyl (5.7 g, 0.015 mol).

The values of elemental analysis of this compound accorded well with its theoretical values as follows:

| Element | Observed value | Theoretical value |
|---------|---------------|-------------------|
| C | 59.5% | 59.54% |
| H | 5.0% | 5.00% |
| N | 14.6% | 14.62% |
| Br | 20.8% | 20.85% |

Further this compound exhibited a C-S point of 174° C. and a smectic phase-isotropic liquid phase transition point (hereinafter abbreviated to S-I point) of 232° C.

EXAMPLE 5

Example 4 was repeated except that 2-(p-bromophenyl)-5-pyrimidinecarboxamidine hydrochloride and α-pentyl-$\beta$ -dimethylaminoacrolein in Example 4 were replaced by 2-(p-fluorophenyl)-5-pyrimidinecarboxamidine hydrochloride and α-propyl-$\beta$ -dimethylaminoacrolein, respectively, to obtain 2-(p-fluorophenyl)-5'-propyl-5,2'-bipyrimidinyl, which exhibited a C-N point of 199° C. and a N-I point of 203° C.

EXAMPLE 6

Example 5 was repeated except that α-propyl-β-dimethylaminoacrolein was replaced by α-butyl-β-dimethylaminoacrolein to obtain 2-(p-fluorophenyl)-5'-butyl-5,2'-bipyrimidinyl. This compound had a melting point of 196° C. and a N-I point of 192° C. This N-I point corresponded to monotropic phase transition point.

EXAMPLE 7

Example 5 was repeated except that α-propyl-β-dimethylaminoacrolein was replaced by β-hexyl-β-dimethylaminoacrolein to obtain 2-(p-fluorophenyl)-5'-hexyl-5,2'-bipyrimidinyl, which exhibited a C-S point of 156° C. and a S-I point of 197° C.

EXAMPLE 8

2-(p-Cyanophenyl)-5'-pentyl-5,2'-bipyrimidinyl

A mixture of 2-(p-bromophenyl)-5'-pentyl-5,2'-bipyrimidinyl (5.0 g, 0.013 mol), N-methyl-2-pyrrolidone (100 mL) and cuprous cyanide (1.16 g, 0.013 mol) was heated under reflux for 5 hours, followed by cooling the reaction mixture down to 40° C., adding toluene (500 ml) and 28% aqueous ammonia (100 ml), separating the resulting layers, washing the toluene layer with water till the washing water became neutral, drying the toluene layer over anhydrous sodium sulfate, distilling off toluene, and three times recrystallizing the residual solids from toluene to obtain 2-(p-cyanophenyl)-5'-pentyl-5,2'-bipyrimidinyl (2.1 g, 0.006 mol).

The values of elemental analysis of this compound accorded well with its theoretical values as follows:

| Element | Observed value | Theoretical value |
|---------|---------------|-------------------|
| C | 72.9% | 72.93% |
| H | 5.8% | 5.81% |
| N | 21.2% | 21.26% |

Further this compound exhibited a C-S point of 186° C. and a S-N point of 264° C.

EXAMPLE 9

A liquid crystal composition (A) consisting of

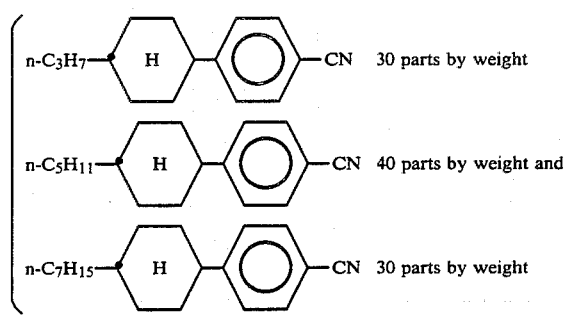

has a N-I point of 52.1° C., a viscosity at 20° C., $\eta_{20}$ of 23.4 cp, a dielectric anisotropy $\Delta\epsilon$ of 11.2 ($\epsilon_{\parallel}=15.9$, $\epsilon_{195}=4.7$), and an optical anisotropy value $\Delta n$ of 0.119 ($n_e=1.609$, $n_0=1.490$) and when the composition was sealed in a TN cell of 10 μm thick, the threshold voltage and saturation voltage were 1.54 V and 2.13 V, respectively.

When 5 parts by weight of 2-(p-pentylphenyl)-5'-propyl-5,2'-bipyrimidine (a compound of the present invention shown in Example 1) were added to 95 parts by weight of the liquid crystal composition (A), the N-I point of the resulting liquid crystal composition rose up to 57.5° C., and $\eta_{20}$, $\Delta\epsilon$ and $\Delta n$ also increased up to 24.1 cp, 11.9 ($\epsilon_{\parallel}=16.9$, $\epsilon_{195}=5.0$) and 0.125, respectively, and when the composition was sealed in the same TN cell, the threshold voltage and saturation voltage were 1.56 V and 2.21 V, respectively.

EXAMPLE 10

When 5 parts by weight of 2-(p-fluorophenyl)-5'-hexyl-5,2'-bipyrimidinyl (a compound of the present invention shown in Example 7) were added to 95 parts by weight of the liquid crystal composition (A) shown in Example 9, the N-I point of the resulting liquid crystal composition rose up to 55.1° C, and also $\Delta\epsilon$ and $\Delta n$ increased up to 13.8 ($\epsilon_{\parallel}=19.4$, $\epsilon_{\perp}=5.6$) and 0.122, respectively. When this liquid crystal composition was sealed in the same TN cell as used in Example 9, the threshold voltage and saturation voltage of the resulting cell were 1.44 V and 2.05 V, respectively.

EXAMPLE 11

When 2 parts by weight of 2-(p-cyanophenyl)-5'-pentyl-5,2'-bipyrimidinyl (a compound of the present invention shown in Example 8) were added to 98 parts by weight of the liquid crystal composition (A) shown in Example 9, the N-I point of the resulting liquid crystal composition rose up to 54.2° C., and also $\Delta\epsilon$ and $\Delta n$ increased up to 11.8 ($\epsilon_{81}=17.1$, $\epsilon_{195}=5.3$) and 0.123, respectively. When this composition was sealed in the same TN cell, the threshold voltage and saturation voltage were 1.32 V and 1.87 V, respectively.

What we claim is:

1. 2,5'-Disubstituted-5,2'-bipyrimidinyls expressed by the formula

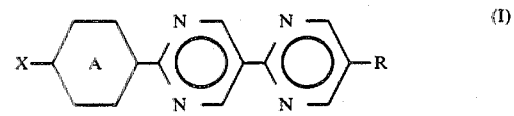

wherein

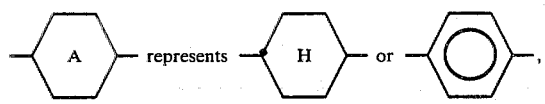

X represents a halogen atom of F, Cl or Br or cyano group or an alkyl group or an alkoxy group each having 1 to 10 carbon atoms and R represents an alkyl group or an alkoxy group each having 1 to 10 carbon atoms.

2. 2-(p-Substituted-phenyl)-5'-alkyl-5,2'-bipyrimidinyls according to claim 1 wherein

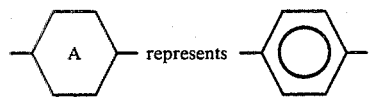

and X is as defined in said formula (I).

3. 2-(Trans-4-alkylcyclohexyl)-5'-substituted-5,2'-bipyrimidinyls according to claim 1 wherein R is as defined above in said formula (I).

4. A liquid crystal composition having at least two components at least one of which is a 2,5'-disubstituted-5,2'-bipyrimidinyl expressed by the formula

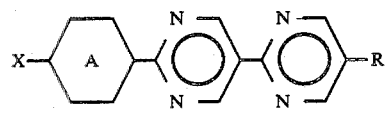

wherein

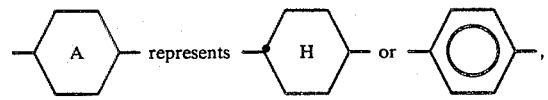

X represents a halogen atom of F, Cl or Br or cyano group or an alkyl group or an alkoxy group each having 1 to 10 carbon atoms and R represents an alkyl group or an alkoxy group each having 1 to 10 carbon atoms.

5. A liquid crystal composition according to claim 4 wherein the content of said 2,5'-disubstituted-5,2'-bipyrimidinyl is 2 to 10% by weight based on the weight of the composition.

* * * * *